United States Patent
Schoelling

(10) Patent No.: US 6,180,051 B1
(45) Date of Patent: *Jan. 30, 2001

(54) METHOD FOR FORMING SHAPED FIBROUS ARTICLES

(75) Inventor: Hans Werner Schoelling, Ennepetal (DE)

(73) Assignee: Johnson & Johnson GmbH (DE)

( * ) Notice: This patent issued on a continued prosecution application filed under 37 CFR 1.53(d), and is subject to the twenty year patent term provisions of 35 U.S.C. 154(a)(2).

Under 35 U.S.C. 154(b), the term of this patent shall be extended for 0 days.

(21) Appl. No.: 08/822,893

(22) Filed: Mar. 24, 1997

(30) Foreign Application Priority Data

Mar. 22, 1996 (DE) ................................................ 196 11 469

(51) Int. Cl.[7] ........................... B29C 43/56; B29C 43/02; B29C 59/16; B29C 69/02
(52) U.S. Cl. ........................... 264/443; 264/296; 264/320; 264/322; 264/69; 264/71; 425/174.2; 425/432; 604/366; 604/384; 28/118
(58) Field of Search ............................... 264/69, 442, 443, 264/71, 296, 320, 322; 425/174.2, 432, 431; 156/73.1; 604/366, 384, 385.1; 28/118, 119

(56) References Cited

U.S. PATENT DOCUMENTS

| | | | |
|---|---|---|---|
| 3,625,787 | 12/1971 | Appleton et al. | 156/73 |
| 3,726,277 | 4/1973 | Hirschman | 128/285 |
| 3,738,364 | * 6/1973 | Brien et al. | 128/285 |
| 3,998,031 | 12/1976 | Kopatz et al. | 53/124 R |
| 4,052,181 | * 10/1977 | Fletcher et al. | 65/2 |
| 4,081,884 | * 4/1978 | Johst et al. | 28/119 |
| 4,195,112 | * 3/1980 | Sheard et al. | 428/288 |
| 4,335,721 | * 6/1982 | Matthews | 128/285 |
| 4,350,649 | * 9/1982 | Summo | 264/23 |
| 4,498,218 | 2/1985 | Friese | 28/119 |
| 4,548,771 | * 10/1985 | Senapati et al. | 264/23 |
| 4,729,175 | * 3/1988 | Beard et al. | 34/1 |
| 4,846,824 | 7/1989 | Lassen et al. | 604/385.1 |
| 4,928,611 | * 5/1990 | Ogawa | 112/217 |
| 4,957,668 | * 9/1990 | Plackard et al. | 264/23 |
| 4,995,150 | 2/1991 | Gerstenberger et al. | 28/119 |
| 5,091,036 | * 2/1992 | Talyor | 156/379.6 |
| 5,153,971 | 10/1992 | Van Iten | 28/118 |
| 5,370,633 | 12/1994 | Villalta | 604/385.1 |
| 5,389,181 | 2/1995 | Vukos et al. | 156/264 |
| 6,003,218 | * 12/1999 | Hull, Jr. et al. | 28/119 |

FOREIGN PATENT DOCUMENTS

| | | |
|---|---|---|
| 33 16 697 A1 | 11/1984 | (DE) . |
| 36 06 150 A1 | 8/1987 | (DE) . |
| 38 04 222 A1 | 8/1989 | (DE) . |
| 161 663 A1 | 11/1985 | (EP) . |
| 162 451 B1 | 8/1991 | (EP) . |
| 546 256 A1 | 6/1993 | (EP) . |
| 0 611 562 A1 | 8/1994 | (EP) . |
| 1418253 | * 12/1975 | (GB) . |
| 2 003 389 | 3/1979 | (GB) . |
| 1 560 736 | 2/1980 | (GB) . |

* cited by examiner

Primary Examiner—Jan H. Silbaugh
Assistant Examiner—Michael I. Poe

(57) ABSTRACT

A method for forming shaped fibrous articles. The method involves introducing at least a portion of a fibrous element into a shaping tool and subjecting the fibrous element in the shaping tool to ultrasonic energy. This imparts the shape of the shaping tool to the surface of the fibrous element. The apparatus has a guide-holder to receive and removably retain a fibrous element and an ultrasonic shaping tool which can be applied to the fibrous element. The shaping tool has a recess corresponding to a predetermined shape for the article. Preferably, the shaping tool and guide-holder are reciprocally moveable with respect to one another.

9 Claims, 1 Drawing Sheet

METHOD FOR FORMING SHAPED FIBROUS ARTICLES

BACKGROUND OF THE INVENTION

The invention relates to a method and device for forming shaped fibrous articles or the like, especially of tampons. In particular, it relates to ultrasonic shaping of fibrous articles.

Fibrous articles, for example, tampons, ear plugs or the like, are formed having a specific shape. Moreover, these fibrous products can be formed of a single type of fiber or of mixed fibers (natural or synthetic). These fibrous products are brought to the desired shape either by rolling or by applying a shaping tool. Thus, for example, a shaping tool having a recess is applied to the tip of a tampon, the recess having the shape to be imparted to the tampon tip. An example of this is shown in Brien et al., U.S. Pat. No. 3,738,364.

An additional prior art shape-forming apparatus is illustrated in FIG. 3. In a conventional shaping device, a tampon 1 having an essentially circular cross-section is held in a guide-holder 2. By means of this guide-holder 2, the tip 3 of the tampon 1 projects beyond the guide-holder 2 and is introduced into a recess 4 of a heated shaping tool 5. The recess 4 has the shape of the desired tampon tip to be produced. The tampon 1 is introduced under pressure into this recess 4, with the result that the fibers in the tip region are compacted. on account of the continuously decreasing cross-section, the friction of the tampon fibers on the surface of the recess 4 increases and the individual tampon fibers are compressed in the tip region, so that the internal friction also rises sharply. It has been shown that the outermost tampon tip is shaped only insufficiently or, as shown in FIG. 3, not at all.

SUMMARY OF THE INVENTION

The object on which the invention is based is to provide a method for forming shaped fibrous articles, for example, tampons, ear plugs, and the like, and an apparatus for forming these articles. The method involves introducing at least a portion of a fibrous element into a shaping tool and subjecting the fibrous element in the shaping tool to ultrasonic energy. This imparts the shape of the shaping tool to the surface of the fibrous element.

The apparatus has a guide-holder to receive and removably retain a fibrous element and an ultrasonic shaping tool which can be applied to the fibrous element. The shaping tool has a recess corresponding to a predetermined shape for the article. The recess has a periphery and an axis orthogonal to the periphery. Preferably, the shaping tool and guide-holder are reciprocally moveable with respect to one another along the orthogonal axis.

DETAILED DESCRIPTION OF THE PREFERRED EMBODIMENT

Figure 1:
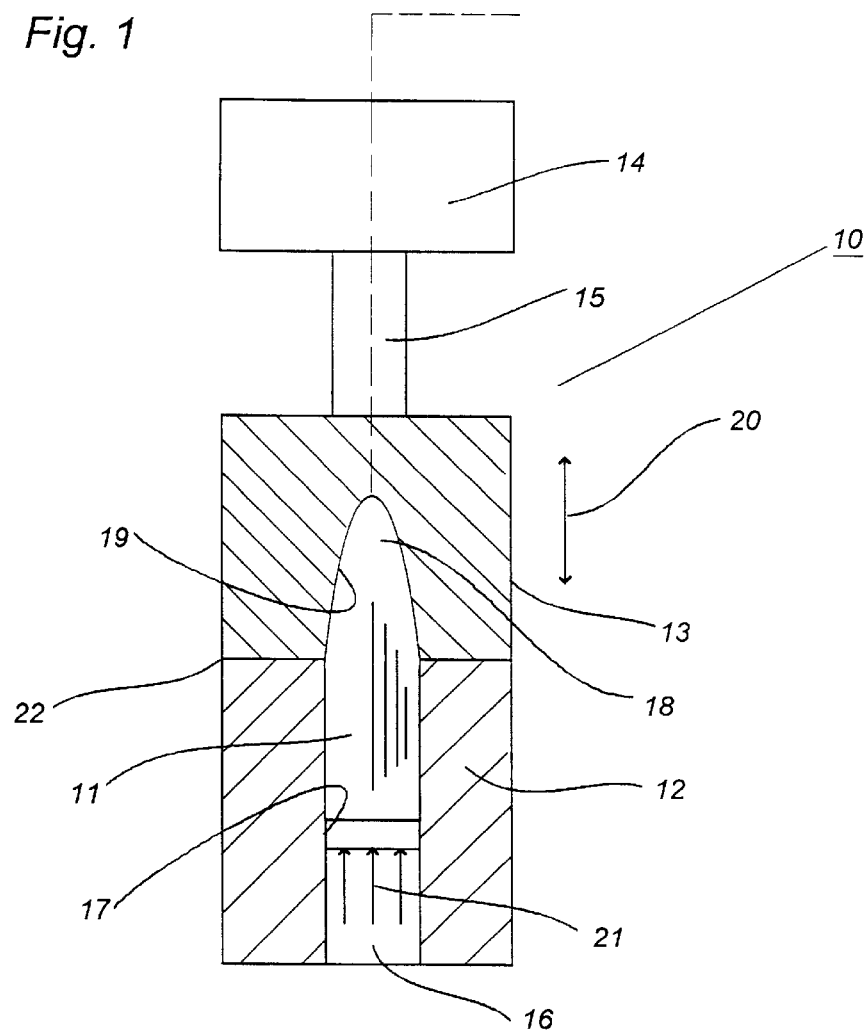
FIG. 1 shows an ultrasonic shaping apparatus according to the present invention.

The invention is described below with reference to a tampon, although the invention is not to be restricted to this example of use, but is to embrace all fibrous or fibrous-like products. According to the invention, the tampon region to be shaped is shaped ultrasonically. This provides the following advantageous effects: (1) by virtue of the action of ultrasound and, if appropriate, simultaneously of a pressing force on the tip of the tampon, heat is generated in this region; (2) moreover, the ultrasonic vibrations cause the individual fibers of the tampon to move more easily past one another to improve shape-forming; (3) furthermore, the ultrasonic vibrations reduce the friction between the wall of the tool and the tampon tip located in the tool; and (4) the heat generated by the ultrasonic vibration gives rise to an ironing or smoothing effect. Due to the improved "flow behavior" of the individual fibers, the present invention provides for much more severe shaping of fibers, for example an elongated, parabolic tampon tip.

According to a preferred feature of the invention, thermal energy in the form of heating or cooling may be supplied to the tampon before, during and/or after the ultrasonic processing to maintain a preferred operating environment. Thus, if sufficient heat to smooth and/or set the fibers is not generated as a result of the pressure and ultrasonic energy, additional thermal energy can be supplied. In contrast, if too much heat is generated by pressure and ultrasonic energy which may damage the fibrous product, the excess heat can be removed by cooling the system. However, additional thermal energy is not always necessary, because an appropriate level of heat may be generated by the application of pressure and ultrasonic energy.

The ultrasonic energy may be applied in any direction to the shaping tool. However, it is preferred that the ultrasonic energy be applied orthogonal to the receiving orifice of the shaping tool. In the case of a tampon, this would be in the axial direction of the tampon.

The preferred embodiment comprises a device which has a guide-holder, for receiving the shank of the tampon, and a shaping tool which is capable of receiving the tip of the tampon. The shaping tool is designed to deliver ultrasonic energy to the fibrous product via at least one recess corresponding to the desired shapes of the fibrous product. Thus, the tampon can be shaped into the finished product in one operation. Of course, the fibrous product may be preformed to bring it into a cylindrical or approximately cylindrical shape. Advantageously, in this case, at least one of the guide-holder and ultrasonic shaping tool is movable relative to the other.

In one embodiment, there is provision for equipping the guide-holder with a sliding means which displaces the tampon in the guide-holder. Via this sliding means, the tampon can additionally be pressed into the ultrasonic shaping tool, for example while the ultrasonic energy is supplied. This may provide pressure on the tampon and therefore on the tampon tip in addition to the ultrasonic energy. It is also possible, however, to push in the tampon further via the sliding means and put it under pressure only after the ultrasonic processing, so that the fibers located on the surface of the tampon tip are compressed.

In a preferred embodiment, an element absorbing ultrasonic vibrations is provided between the free end face of the ultrasonic shaping tool and that end face of the guide-holder which faces the ultrasonic shaping tool. During the ultrasonic processing, this element allows a guide-holder to exert pressure over its entire area on the ultrasonic shaping tool, without the vibrations of the ultrasonic shaping tool being transmitted to the guide-holder. In a preferred embodiment, the ultrasonic shaping tool has a vibration frequency of up to about 35 kHz and/or an amplitude of about 50 to about 100 microns, more preferably about 80 microns.

For the simultaneous processing of a plurality of tampons, the ultrasonic shaping tool may have a plurality of recesses. In this case, the ultrasonic shaping tool is designed so that the introduction of energy into the individual tampons is distributed uniformly. In addition, a more complex, single fibrous product may be formed using an ultrasonic shaping tool having a plurality of recesses, or complex recesses.

Further advantage, features and particulars of the invention emerge from the following description which, with reference to the drawing, represents in detail an especially preferred embodiment. At the same time, the features in the drawing and mentioned in the claims of the description can be essential to the invention each individually in themselves or in any combination.

Referring to FIG. 1, the present invention includes a shaping device, designated as a whole by 10, which has a guide-holder 12 for the tampon 11 to be shaped. This guide-holder 12 is operatively connected to an ultrasonic shaping tool 13. The ultrasonic shaping tool 13 is transmits ultrasonic energy supplied by a converter 14 through a transformer 15. Moreover, the guide-holder 12 has a sliding means 16 which is arranged displaceably in the orifice 17 of the guide-holder 12.

The tampon 11 to be shaped is inserted into this orifice 17, so that its tip 18 to be shaped projects beyond the guide-holder 12. Subsequently, at least one of the guide-holder 12 and the ultrasonic shaping tool 13 are moved with respect to the other to introduce the tip 18 a recess 19 of the ultrasonic shaping tool 13. The ultrasonic shaping tool 13 is then set in vibration, an indicated by the double arrow 20. At the same time, the surface friction between the recess 19 and fibers of the tampon 11 and the mutual friction of the individual fibers are greatly reduced, so that the tip 18 Of the tampon 11 adapts to the shape of the recess 19 and assumes this shape. Simultaneously, heat is supplied to the tampon tip 18 via the ultrasonic shaping tool 13.

Either this heat can be introduced externally (applied thermal energy) or it is generated during the ultrasonic processing (ultrasonic energy). Furthermore, during the ultrasonic processing, the tampon 11 can be further compressed by moving the sliding means 16 as indicated by arrows 21. Thus, the tampon tip 18 can be better forced into the recess 19. The sliding means 16 can be actuated during ultrasonic processing and/or also after the conclusion of ultrasonic processing, which lasts from between about 0.2 and about 5 seconds, preferably about 0.5 seconds. An element 22 absorbing ultrasonic vibrations is located between the guide-holder 12 and the ultrasonic shaping tool 13, so that, even during ultrasonic processing the guide-holder 12 can touch the ultrasonic shaping tool 13 and nevertheless substantially all of the ultrasonic energy is introduced into the tampon 11 or its tip 18. The pressing of the fibers of the tampon tip 18 onto the hot surface of the recess 19 gives rise to an ironing effect and to a compression of fibers.

Figure 2:
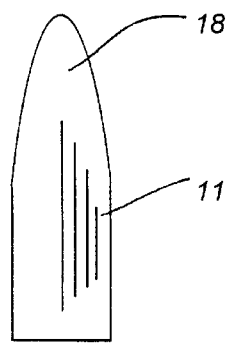
FIG. 2 shows a shaped fibrous article formed in the ultrasonic apparatus of FIG. 1.
Figure 3:
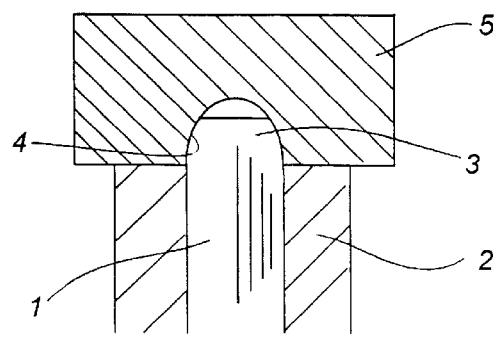
FIG. 3 shows a device for the shaping of fibrous articles according to the prior art.

As shown in FIG. 2, the apparatus and method can produce tampons 11 which have, for example, a parabolic tip. In contrast to a conventional hemispherical tip, this parabolic tip 18 has a cross-section which changes over a much longer length. Thus, conventional shaping methods may be unsuitable.

What is claimed is:

1. A method for forming a shaped fibrous article comprising the steps of:
   (a) preforming a fibrous product into a shaped fibrous element;
   (b) introducing, under pressure, at least a portion of the fibrous element into a shaping tool having a recess; and
   (c) subjecting the at least a portion of the fibrous element in the shaping tool to ultrasonic vibrations wherein individual fibers of the at least a portion of the fibrous element move more easily past neighboring fibers to form the at least a portion of the fibrous element into a predetermined shape corresponding to the recess of the shaping tool while heat generated by the ultrasonic vibrations causes ironing of the at least a portion of the fibrous element to thereby form the shaped fibrous article.

2. The method of claim 1 further comprising subjecting the fibrous element to thermal energy.

3. The method of claim 1 comprising inserting the fibrous element into the shaping tool while subjecting the fibrous element to ultrasonic vibrations.

4. The method of claim 1 further comprising compressing the fibrous element in the shaping tool.

5. The method of claim 1 wherein the shaping tool has a major axis and the ultrasonic vibrations are directed along the major axis.

6. The method of claim 1 wherein the ultrasonic vibrations have a frequency of up to about 35 kHz.

7. A method for forming a tampon comprising the steps of:
   (a) preforming a fibrous product into an approximately cylindrically shaped fibrous element to form a tampon preform;
   (b) introducing, under pressure, at least a portion of the tampon preform into a shaping tool having a recess; and
   (c) subjecting the at least a portion of the tampon preform in the shaping tool to ultrasonic vibrations wherein individual fibers of the at least a portion of the tampon preform move more easily past neighboring fibers to form the at least a portion of the tampon preform into a predetermined shape corresponding to the recess of the shaping tool while heat generated by the ultrasonic vibrations causes ironing of the at least a portion of the tampon preform to thereby form the tampon.

8. A method for forming a fibrous article selected from the group consisting of tampon and earplug, the method comprising the steps of:
   (a) preforming a fibrous product into a shaped fibrous element;
   (b) introducing, under pressure, at least a portion of the fibrous element into a shaping tool having a recess; and
   (c) subjecting the at least a portion of the fibrous element in the shaping tool to ultrasonic vibrations wherein individual fibers of the at least a portion of the fibrous element move more easily past neighboring fibers to form the at least a portion of the fibrous element into a predetermined shape corresponding to the recess of the shaping tool while heat generated by the ultrasonic vibrations causes ironing of the at least a portion of the fibrous element to thereby form the shaped fibrous article.

9. A method for forming an earplug comprising the steps of:
   (a) preforming a fibrous product into a shaped fibrous element to form an earplug preform;
   (b) introducing, under pressure, at least a portion of the earplug preform into a shaping tool having a recess; and (c) subjecting the at least a portion of the earplug preform in the shaping tool to ultrasonic vibrations wherein individual fibers of the at least a portion of the earplug preform move more easily past neighboring fibers to form the at least a portion of the earplug preform into a predetermined shape corresponding to the recess of the shaping tool while heat generated by the ultrasonic vibrations causes ironing of the at least a portion of the earplug preform to thereby form the earplug.

* * * * *